United States Patent [19]

Snow et al.

[11] Patent Number: 4,796,639

[45] Date of Patent: Jan. 10, 1989

[54] PULMONARY DIAGNOSTIC SYSTEM

[75] Inventors: Michael G. Snow, North St. Paul; William R. Tyler, St. Paul; Sung-Peng Hsu, Eagan, all of Minn.; Robert J. Fallat, San Rafael, Calif.

[73] Assignee: Medical Graphics Corporation, St. Paul, Minn.

[21] Appl. No.: 117,482

[22] Filed: Nov. 5, 1987

[51] Int. Cl.⁴ .......................... A61R 5/08; G06F 15/42
[52] U.S. Cl. .................................. 128/719; 128/671; 128/725; 364/413.02
[58] Field of Search ............... 128/719, 725, 671, 730, 128/716; 364/415, 413.02

[56] References Cited

U.S. PATENT DOCUMENTS

| | | | |
|---|---|---|---|
| 4,106,503 | 8/1978 | Rosenthal et al. | 128/203.12 |
| 4,121,583 | 10/1978 | Chen | 128/203.27 |
| 4,267,845 | 5/1981 | Robertson, Jr. et al. | 128/721 |
| 4,296,756 | 10/1981 | Dunning et al. | 128/725 |
| 4,463,764 | 8/1984 | Anderson et al. | 128/719 |
| 4,484,577 | 11/1984 | Sackner et al. | 128/203.28 |

OTHER PUBLICATIONS

Ellis, Perera & Levin (Chest vol. 68: pp. 209-213, 1975).
Fallat & Snow (Comp. Med. vol. II, No. 3: pp. 14-18, 1984).
Geddes, Green & Emerson (Thorax, vol. 33, pp. 257-260, 1978).
Cary, Huseby, Culver & Kosanke (Chest vol. 76: 4, Oct. 1979).
American Review of Respiratory Disease, vol. 106, 1972, pp. 614-617.
Aikins (Heuristic Programming Project, Computer Science Department, Stanford University, Jul. 1979).
Kinney (Chest vol. 91: Jan. 1987, pp. 3-4.

Primary Examiner—A. Michael Chambers
Attorney, Agent, or Firm—Orrin M. Haugen; Thomas J. Nikolai; Frederick W. Niebuhr

[57] ABSTRACT

A pulmonary diagnostic apparatus includes a personal computer including a memory for storing expected values, each representing a predicted normal level for a pulmonary function. A parameter limit file stores abnormality limits, each related to one of the expected values. A configuration file contains a plurality of degree of severity labels and numerical breakpoints between severity degrees. Finally, a statement data file contains a plurality of textual statements concerning lung functions and diseases or conditions. The three files are operatively associated with the computer. Lung function measuring equipment also is connected to the computer, whereby measured values are compared with the expected values. Based on the comparison, the computer generates an output identifying certain measured values as abnormal, and the degree of abnormality. Also, appropriate statements from the statement data file are generated as output, based upon the comparison. By selectively editing the parameter limit, configuration and statement files, the operator can cause the computer to generate an output corresponding to the operator's preferred analytical approach and syntax.

16 Claims, 3 Drawing Sheets

PULMONARY DIAGNOSTIC SYSTEM

BACKGROUND OF THE INVENTION

This invention relates to medical diagnostic apparatus, and more particularly to a computer based system for pulmonary diagnosis based on measured performance of the lungs during selected testing.

The use of computer based systems in forming medical diagnoses, and more particularly in diagnosing pulmonary function, is well known. Evaluation of pulmonary condition involves measurement of the size of the lungs, the limitation to air flow, e.g. flow rates, the adequacy of gas exchange (diffusion), and response to aerosol drugs (bronchodilator response). Such pulmonary function testing typically generates up to sixty parameters for evaluation. Manual examination of the results of such testing is tedious and time consuming. A computer program for calculating and interpreting standard pulmonary function test data is disclosed by Ellis, Pareja and Levin in 1975 (Chest Volume 68: Pages 209–213, 1975). This and like systems were directed principally to identifying abnormal parameters. While diagnosis can be simplified by focusing on key parameters, this increases the risk of overlooking subtle anomalies.

As disclosed by Fallat and Snow (Comp. Med. Volume II, No. 3: Pages 14–18, 1984), a program designated "Micropuff" has been developed in an effort to mirror a clinician's approach to analyzing pulmonary function data, utilizing a personal computer. The Micropuff program aids interpretation by first identifying various parameters among those tested as abnormal, and then applying abnormality flags to a set of rules for generating conversational text, tailored to the individual physician. Diagnostic statements generated as a result of this analysis are subject to final correction by or for the physician, for example through conventional word processing techniques. Fallat and Snow reported the results of testing, in which seventy-five percent of the computer generated interpretations were accepted without modification. Further, substantial time is saved because the physician edits, rather than creates, the diagnostic text.

While the Micropuff program has been successful in certain respects, it also has shed light on the need to tailor pulmonary diagnostic systems to the interpretation habits and syntax of individual physicians. Moreover, the same physician may wish to interpret pulmonary function test parameters based on different approaches tailored to special situations, for example epidemiology studies.

Therefore, it is an object of the present invention to provide a pulmonary function analysis system which can be modified by the physician in accordance with his or her analytical approach.

Another object of the invention is to provide pulmonary function diagnostic apparatus for identifying selected pulmonary function parameters as abnormal, and further for identifying the degree or extent of abnormality, in accordance with values predetermined by the physician.

Yet another object is to provide a pulmonary analysis system for generating preliminary diagnoses of pulmonary function, including textual statements, wherein the bases for selecting among the textual statements, and content of the statements themselves, are subject to physician modification.

SUMMARY OF THE INVENTION

To achieve these and other objects, there is provided a diagnostic apparatus including a first electronic data storage means, and a plurality of expected values stored in the first data storage means, each expected value representing a predicted normal level for a pulmonary function. The apparatus also includes a first data input means for entering a plurality of expected value ranges into the first data storage means. Each range corresponds to and encompasses one of the expected values. The first data input means includes user operable range input means for adjustably determining the range corresponding to each expected value. Consequently each range represents a pulmonary function at a level within a normal range as determined by the user. A second data input means is provided for entering a plurality of boundary values into the first data storage means. The boundary values are arranged in sets of consecutively increasing value, with each set corresponding to one of the ranges and determining, with respect to the corresponding range, increasing degrees of departure from the range. The second data input means includes user operable boundary input means for adjustably determining the boundary values. As a result, the degrees of departure corresponding to each range are determined by the physician, and represent a pulmonary function at increasingly abnormal levels as determined by the physician or user. A pulmonary function testing means measures a plurality of pulmonary functions and provides a plurality of performance values to the first data storage means. Each performance value is based upon a measured pulmonary function and corresponds to one of the expected values. A processing means, operatively associated with the first data storage means, compares each performance value with its corresponding value range, and generates a first output indicating whether or not the performance value is within the corresponding range. The processing means also compares each performance value lying outside of its corresponding range with its corresponding set of boundary values, and generates a second output indicating a degree of departure from the corresponding range. A display means, operatively associated with the processing means, presents the first and second outputs in a form to facilitate user recognition.

Preferably each range is determined by upper and lower limits respectively greater than and less than the corresponding predicted value. Degrees of departure can then be defined by preselected increasing, discrete levels for a quantity B determined in accordance with the following formula:

$$B = 10(1 - M/L)$$

where B is the extent of the departure, M is a measured performance value, and L is one of the upper or lower limits, specifically the one nearest the measured performance value.

A second data storage means can be provided for storing a plurality of degree of severity labels, each corresponding to one of the degrees of departure. Preferably a data entry means is connected with the second storage means and operable by the physician for modifying the degree of severity labels. The processing means then selects one of the severity labels in accordance with the determined degree of departure, and generates the selected label as the second output.

A third storage means can be provided for storing a plurality of pulmonary condition diagnostic labels. Then, the processing means generates the second output by providing one of the diagnostic labels and one of the degrees of severity labels, both selected in accordance with particular ones of the measured performance values outside of their associated ranges, and the degree of severity for each of the particular measured values.

A fourth storage means can include a plurality of textual statements of pulmonary condition. The processing means selects at least one selected statement from the available statements in accordance with the particular ones of the measured performance values outside of their associated ranges and the degree of abnormality of each particular measured performance value. The data entry means is usable to selectively modify the textual statements. The textual statements can relate either to the normality or abnormality of pulmonary function such as total lung capacity, forced expiratory volume, or residual volume, or to general pulmonary conditions or diseases, such as obstructive airways disease or a type of such disease such as emphysema.

Thus, in accordance with the present invention, a physician can select the size of the "normal" range about a normal expected value for each measured parameter. The physician can define ranges, beyond the normal range, of stepped degrees of abnormality, and designate a label corresponding to each degree and describing the abnormal condition, e.g. mild, moderately severe, or severe. Finally, textual statements may be modified, for example to change "obstructive airways disease" to "obstructive airways defect", or to change "is normal" to "is within normal limits. Thus, apparatus in accordance with the present invention substantially enhances the computer assisted analysis of pulmonary function data, in that the analysis can be modified in accordance with an individual physician's analytical approach and syntax.

IN THE DRAWINGS

For a better appreciation of the above and other features and advantages, reference is made to the following detailed description and drawings, in which.

DETAILED DESCRIPTION OF THE PREFERRED EMBODIMENT

Figure 1:
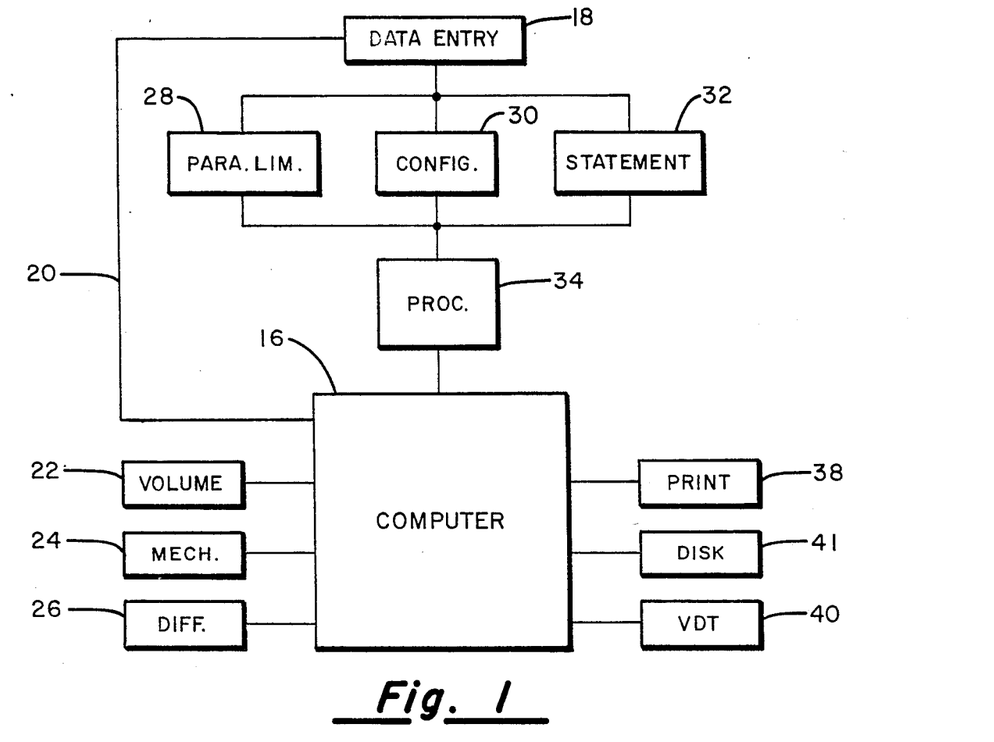
FIG. 1 is a block diagram of a pulmonary function analysis system constructed in accordance with the present invention.

Turning now to the drawings, there is shown in FIG. 1 a system for measuring parameters of pulmonary function, and generating a preliminary diagnosis of pulmonary condition, based upon comparison of measured parameters with expected values for such parameters. At the heart of the system is a central computer 16, which can be a personal comptuer, for example an IBM AT personal computer. Computer 16 receives and stores data from a number of sources, including a data entry device 18, preferably a keyboard operatively connected to the computer over a line 20. Data entered over line 20 includes preliminary information prior to testing an individual patient, for example the expected values for a multiplicity of parameters reflecting normal levels for pulmonary functions and conditions, for example air flows and lung volumes, based on the patient's age, height and sex.

The system includes lung measurement equipment for providing data to computer 16 during testing of the patient. A volume measuring device 22, for example a plethysmograph nitrogen wash-out circuit, measures and provides the computer with lung volume parameters such as slow vital capacity (SVC), residual volume (RV), thoracic gas volume (TGV), total lung capacity (TLC), and alveolar volume (VA).

Lung mechanics parameters are measured and provided to the computer by a mechanics measuring device 24, typically a spirometer or flow device. Parameters measured by the spirometer include forced vital capacity (FVC) measuring vital capacity performed with a maximally forced expiratory effort, forced expiratory volume ($FEV_T$ where T is the number of seconds of FVC), forced expiratory flow ($FEX_X$ where X is the amount of FVC exhaled when the measurement is made), and airway resistance ($R_{AW}$). Diffusion measuring equipment 26, for example a gas chromatograph, measures and provides the lung diffusing capacity ($DL_{CO}$), based on a single breath or steady-state measurement.

Data entry device 18 also provides information for storage in a number of data files, including a parameter limit file 28, a configuration file 30 and a statement file 32. These files, in turn, provide such information to a processor 34 operatively connected to computer 16.

The output of computer 16 is provided to a printer 38, a video display terminal 40 and a data storage medium such as a disk drive 41. The display terminal permits the physician or other user to monitor preliminary diagnostic results during testing, while the printer provides the same results in permanent form. These results include the measured parameters, the identification of particular parameters, if any, falling outside of a chosen range for normal and therefore identified as "abnormal", and textual statements, e.g. that the lung functions are normal, or that an obstructive airways disease, for example asthma, is indicated. A diagnosed disease or any other abnormal condition can be further identified as to degree of severity.

A significant problem with prior art pulmonary diagnostic systems, particularly computer enhanced systems, stems from the tendency in individual experts to interpret the same data in different ways. Two physicians may disagree as to whether a certain parameter is "abnormal", or as to whether an abnormality is insignificant, or sufficiently severe to merit attention. Names identifying various pulmonary conditions vary among physicians and among different regions of the country.

In accordance with the present invention, a preliminary diagnosis can be tailored in accordance with individual preferences and styles of physicians or other experts. More particularly, data files 28, 30 and 32 are all subject to modification, with changes effected conveniently by the user through keyboard 18.

Parameter limit file 28 stores a plurality of abnormality limits, each limit related to a parameter. The parameter may correspond to a normal value for a pulmonary function or condition, or may reflect the relationship between or among two or more such values, for example diffusing capacity divided by alveolar volume. The following Table I is exemplary of the type of data stored in parameter limit file 28:

TABLE I

PARAMETER ABNORMALITY LIMITS

| Lung Mechanics | | |
|---|---|---|
| FVC | (l) | 2.0 |
| FEV | (l) | 2.0 |
| FEV$^1$ | (l) | 2.0 |
| FEV$^3$/FVC | (%) | 0.2 |
| FEF$^1$ - 50% | (l/sec) | 2.0 |
| FEF - max | (l/sec) | 2.0 |
| Lung Volumes | | |
| SVC | (l) | 2.0 |
| RV (n$_2$) | (l) | 3.0 |
| TLC (n$_2$) | (l) | 2.0 |
| RV (pleth) | (l) | 2.0 |
| TLC (pleth) | (l) | 2.0 |
| TGV (pleth) | (l) | 2.0 |
| R$_{aw}$ | | 2.0, 0.2–2.5 |
| Diffusing Capacity | | |
| DL$_{co}$ | (ml/min/mmHg) | 2.0 |
| Alveolar volume | (l) | 2.0 |
| TLC (SB) | (l) | 2.0 |
| Blood Gases | (Torr.) | 2.0 |
| P$_a$O$_2$ | | |

Other parameters may be included in file 28, the above being exemplary. The data is arranged in three columns, with the first (left) column identifying the parameter by its recognized acronym, the second column identifying the units of measurement, and the third column identifying the abnormality limit. For each of the parameters, processor 34 utilizes the abnormality limit to define a normal range about an expected value of that parameter, in accordance with the following formulas:

$$LL = P \times (10 - A)/10$$

$$UL = P \times (10 + A)/10$$

where LL is the lower limit of the normal range, UL is the upper limit, P is the predicted or expected value of the parameter, and A is the abnormality limit from the third column. Thus, for an abnormality limit of 2.0, LL is 80% of P, and UL is 120% of P.

It is the physician or other expert, selecting abnormality limits through keyboard 18, who establishes the normal range for each parameter, based upon what he or she considers an acceptable normal range about a given expected parameter.

Configuration file 30 is used by processor 34 along with the parameter limit file. The configuration file contains data in accordance with the following Table II:

TABLE II

CONFIGURATION FILE

| no significant | bronchodilator response label |
| a slight | bronchodilator response label |
| a good | bronchodilator response label |
| an excellent | bronchodilator response label |
| minimal | degree of severity label |
| mild | degree of severity label |
| moderate | degree of severity label |
| moderately severe | degree of severity label |
| severe | degree of severity label |

TABLE II-continued

CONFIGURATION FILE

| 0.0 | degree breakpoint |
| 1.0 | degree breakpoint |
| 2.0 | degree breakpoint |
| 3.0 | degree breakpoint |
| 4.0 | degree breakpoint |

The configuration file can further provide for selecting normal ranges based on standard deviation rather than on percent, and for selecting the automatic system as opposed to a manual option.

All entries in the lefthand column of Table II can be modified using keyboard 18. The first four entries are possible descriptions for a measured improvement in lung performance, following administration of a bronchodilator. The remaining entries are related to the contents of parameter limit file 28, in that once a measured parameter (or a calculated parameter based upon measured values) is found to be outside of the expected normal range, its degree of abnormality is determined in accordance with the breakpoint values in configuration file 30. The degree of abnormality or extent of departure from normal is determined in accordance with the formula:

$$B = 10(1 - M/L)$$

where B is the extent of departure, M is the measured performance value and L is the particular one of the upper and lower limits (UL and LL) which is nearest to the measured performance value. The degree of severity labels are selected based on a comparison of the quantity B with the degree breakpoints. For example, in accordance with Table II, if the quantity B is greater than 0 and up to 1.0, the abnormality is defined as "minimal", while if B is between 3.0 and 4.0, the abnormality is labeled "moderately severe".

Accordingly, using keyboard 18 the physician can interchange labels, for example substituting "no substantial" for "no significant", or by changing one or more breakpoints. And, given the dependence of the breakpoint formula upon values for the upper and lower limits of the normal range, the physician in effect modifies the breakpoints when he or she modifies an abnormality value.

Statement file 32 contains a "dictionary" of numbered textual statements relating to pulmonary function or condition, and related diagnostic information. The following Table III includes exemplary entries:

TABLE III - STATEMENT DICTIONARY

1. Lung volumes are within normal limits.
5. The TLC, FRC and RV are increased indicating over-inflation.
6. The lung volumes are reduced.
27. Following administration of bronchodilators, there is _*_ response.
51. There is excess variability between efforts which makes it impossible to adequately evaluate the flow volume loops.
55. The FVC, FEV$_1$, FEV$_1$/FVC ratio, and FEF 25–75% are reduced indicating airway obstruction.
64. The reduced diffusing capacity indicates a _*_ loss of functional alveolar capillary surface.
109. _*_ airway obstruction and overinflation are present.

121. The MVV is reduced more than the FEV$_1$ suggesting poor effort or concurrent neuromuscular disease.
163. The TLC determined by plethysmography is inconsistent with the values obtained by nitrogen washout and the diffusing capacity. Re-assessment of the plethysmography value is suggested.
164. The alveolar volume determined by the single breath diffusing capacity is larger than the total lung capacity. Reassessment of lung volume measurements is suggested.

*: Replaced with a selected bronchodilator response label or severity label from Table II As seen from the above exemplary statements, statement file 32 contains a variety of types of statements, including simple statements as to the normality or abnormality of given parameters, relating to preliminary diagnoses of conditions such as obstructed airways, and even statements suggesting further testing based on lack of complete or incongruous results. Statement file 32 also includes diagnostic labels for pulmonary condition, for example normal pulmonary function, asthma, bronchitis, etc. Processor 34 selects one or more labels from statement file 32 in accordance with the settings in data files 28 and 30, and pursuant to preselected algorithms as is later explained.

With expected parameter data appropriate to a particular patient entered into computer 16, and with data files 28, 30 and 32 modified in accordance with the preference of the physician, the patient is instructed alternatively to breathe normally and in a forced manner, and lung function and performance are measured with measurement equipment 22, 24 and 26. The output of the equipment is provided to computer 16, thus to generate actual or measured parameters. Processor 34 compares the measured parameters with the previously stored expected parameters, determining abnormality and degree of abnormality in accordance with data files 28 and 30, and providing to computer 16 selected statements from data file 32 in accordance with abnormality and degrees of abnormality, for output to printer 38, disk drive 41 and display terminal 40.

Figure 2:
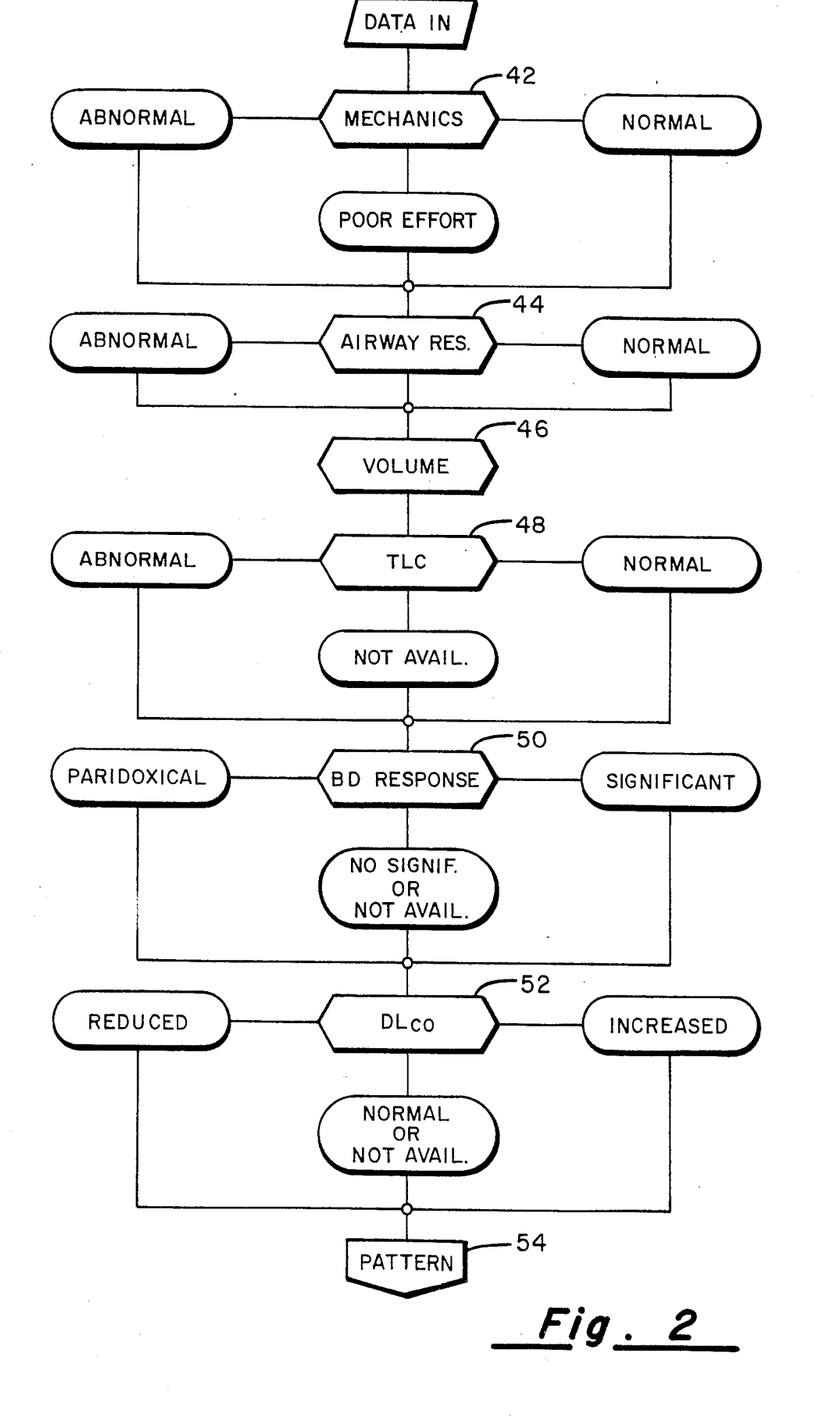
FIGS. 2, 3 and 4 are flow charts illustrating the analysis of pulmonary function parameters utilizing the system of FIG. 1.

In accordance with this method, the first step performed by processor 34 is the detection of abnormalities, illustrated in FIG. 2. Measured pulmonary data are evaluated in sequence, with spirometry data evaluated first as indicated at 42. The evaluation consists of comparing each parameter with its corresponding predicted value to determine whether it lies within or outside of the corresponding normal range, as predetermined by the physician when selecting the abnormality limit. At this stage for example, the following lung mechanics parameters may be evaluated: FVC (forced vital capacity), FEV$_t$ (timed forced expiratory volume, where t is the time in seconds of FVC), FEF$_x$ (forced expiratory flow, where x is the portion of percentage of the FVC curve), and MVV (maximal voluntary ventilation). Each of these parameters is evaluated as either normal or abnormal. If all variables are within their corresponding normal ranges, a normal statement is generated. Alternatively, a poor effort is indicated. Then the process moves to the next stage. An absence of data in any given stage also results in a move to the next category.

At the next stage, one more lung mechanics parameter, R$_{aw}$ (airway resistance), is evaluated individually at 44. If measured airway resistance is greater than the upper limit of normal, then the abnormal indication is given, while if the measured value is equal to or less than the upper limit of normal, then the normal statement is the result.

As indicated at 46, the method for determining volume data is noted for further evaluation if necessary, particularly as to whether the methodology is plethysmography, nitrogen washout, or single breath diffusion.

At the next stage, lung volume parameters are evaluated as indicated at 48. The volume parameters include TLC (total lung capacity), SVC (slow vital capacity), FRC (functional residual capacity), and RV (residual volume). Relationships between parameters are also evaluated, for example RV/TLC and FEV$_1$/FVC. The lung volume parameters are evaluated as abnormally high, abnormally low, or normal, provided that measurements have been taken and a statement is available.

The next stage, indicated at 50, occurs only if a bronchodilating medication is administered during testing, and involves a re-measurement of previously indicated parameters following such administration. A significant response is indicated if pulmonary function experiences marked improvement after bronchodilator administration, while a paradox is indicated if performance is shown as worse after administration. The other optional result based on actual data is an indication of no significant response to the administration of a bronchodilator. Lung mechanics parameters re-evaluated at this stage include FVC, FEV$_1$, FEV$_3$, FEF (25-75%), TLC and R$_{aw}$.

Diffusion is evaluated at 52 using DL$_{CO}$ (corrected for hemoglobin if available), alveolar volume and the ratio of DL to alveolar volume (DL/VA). Differences between alveolar volume measured during single breath diffusing capacity procedure are compared with nitrogen wash-out or plethysmography measurements of TLC. Diffusion is evaluated and reported as increased, decreased or normal.

Thus, in accordance with the process illustrated in FIG. 2, processor 34 compares previously stored parameters with measured data to generate a series of flags identifying various parameters as either normal or abnormal. Further, however, processor 34 generates a clinical pattern evaluation at 54, shown in greater detail in the flow chart of FIGS. 3 and 4. A significant feature of the present invention resides in the reevaluation of primary flags based on the presence of multiple abnormalities, determined in accordance with the flow charts of FIGS. 3 and 4.

Figure 3:
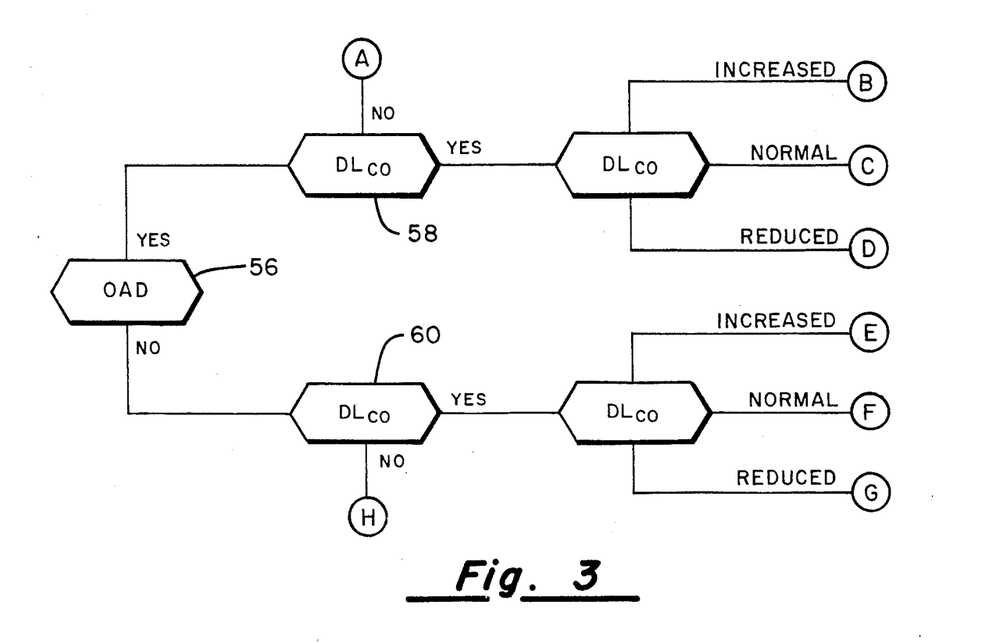
Figure 4:
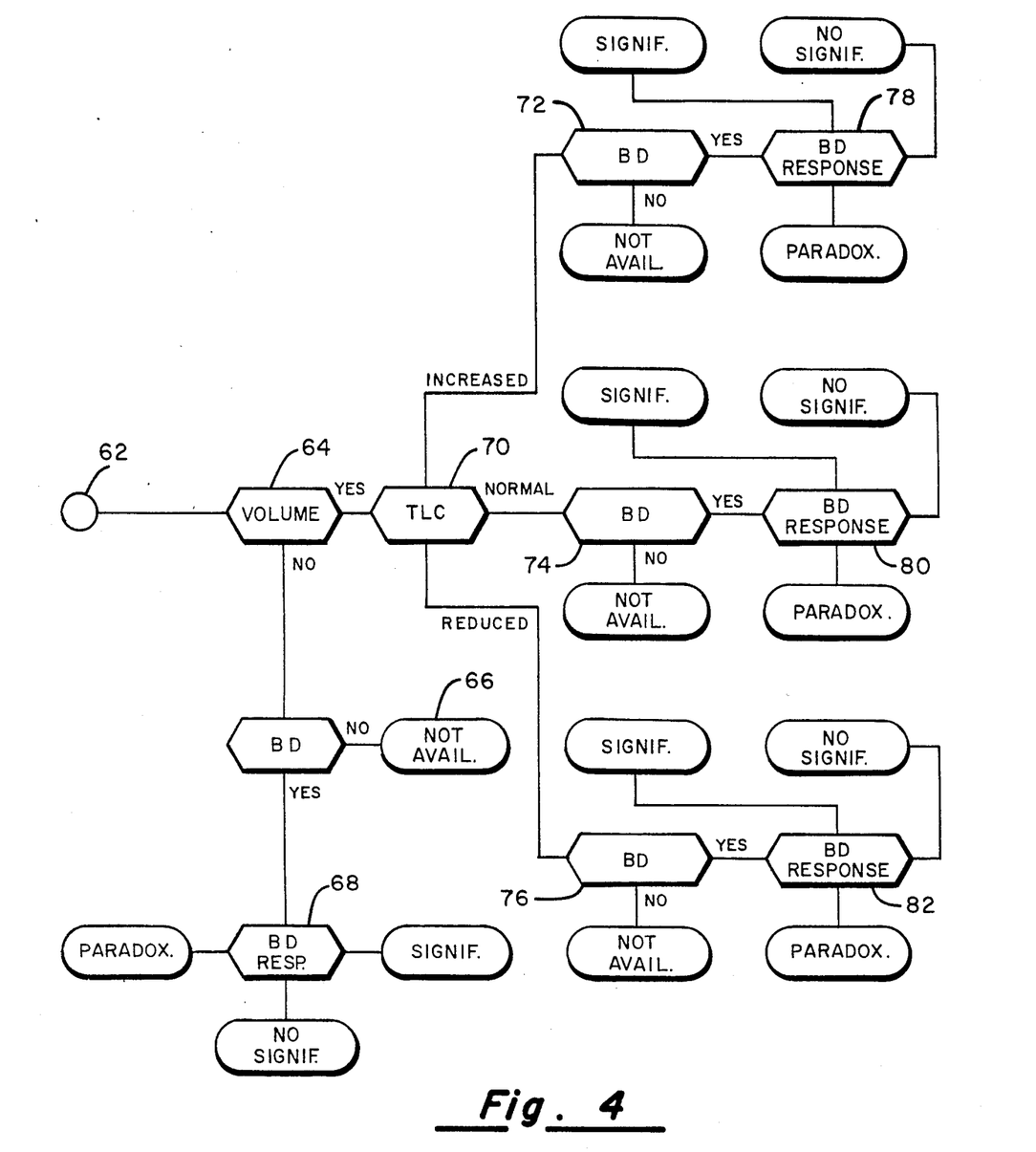

The first step in clinical pattern evaluation is identifying the presence of obstructive airways disease (OAD). The presence of OAD and its degree of severity are determined in accordance with the following formula:

OAD degree = FEV$_1$/FVC + (FEF 25-75%/5) + (FEF 75%/20)

The degree of severity number (breakpoint) from data file 30 is used for each quantity in this equation, e.g. FEV$_1$/FVC will equal 1, 2, 3 or 4 if abnormality is found and the breakpoints are set as indicated in Table II above. Of course, if FEV$_1$/FVC was found to be normal, its severity degree is 0. As indicated in FIG. 3, the pattern evaluation process proceeds along one of two paths from an obstructed airways disease (OAD) decision 56, depending upon whether OAD is indicated. While the above mathematical algorithm for OAD is preferred, the scope of this invention includes alternative algorithms.

In either event, the next step is to indicate whether or not diffusion measurements were taken during testing, as indicated respectively at 58 and 60. If not, the alternative outputs are A and H, depending upon whether OAD was previously indicated. If measurements were taken, the final indication or resultant in FIG. 3 is based on whether the diffusion is normal, increased, or reduced. Thus, the resultant of FIG. 3, which is provided as the input to the program portion shown in FIG. 4 at 62, can be one of eight alternatives as indicated at Table IV:

TABLE IV

| | |
|---|---|
| A | no $DL_{CO}$, OAD |
| B | increased $DL_{CO}$, OAD |
| C | normal $DL_{CO}$, OAD |
| D | reduced $DL_{CO}$, OAD |
| E | increased $DL_{CO}$, no OAD |
| F | normal $DL_{CO}$, no OAD |
| G | reduced $DL_{CO}$, no OAD |
| H | no $DL_{CO}$, no OAD |

The resultant, i.e. one of A−H, is re-evaluated as to whether lung volume measurements were taken during testing, at 64. If not, and if no bronchodilator was administered, a statement to that effect is indicated as at 66. If a bronchodilator was administered, then a BD response at 68 is evaluated, with one of three resultants, i.e. either a significant response, no significant response, or a paradoxical response to the bronchodilator.

Alternatively, if lung volume measurements were taken (the "YES" output of evaluation 64), total lung capacity is reevaluated at 70 for an indication that it is increased, normal or reduced. Then, the presence of data following bronchodilator administration is assessed in each case at 72, 74 and 76, respectively, and the nature of the bronchodilator response is evaluated at 78, 80 and 82, respectively, yielding one of the three results explained in connection with the evaluation at 68.

To summarize, the pattern recognition illustrated in FIGS. 3 and 4 proceeds as follows:
(1) Is OAD indicated?
(2) Were diffusion measurements obtained?
    If so, is diffusion normal, increased, or reduced?
(3) Were lung volume measurements obtained? If so, are volume parameters normal, increased, or reduced?
(4) Was a bronchodilator administered? If so, was the response significant, not significant, or a paradox?

Pattern recognition and initial abnormality detection (FIG. 2) are preferably accomplished by processor 34, programmed in accordance with computer programming techniques known to those skilled in the art.

To further explain the pattern evaluation of FIGS. 3 and 4, the following examples are presented, each corresponding to the examination of a particular patient.

EXAMPLE I

MEDICAL GRAPHICS
350 OAKGROVE PARKWAY
ST. PAUL, MN 55110
Name: CONSULT    Date: 1/17/86    ID: 119
Age: 47 yr    Sex: M    Height: 175.00 cm    Weight: 101.00 kg
Dr.    Technician:    Room: OP
Pack Years: 15 yr    Years quit: 10 yr    Packs/Day: 0.00
Dyspnea History: Only ofter Severe exertion
Diagnosis:    CHRONIC BRONCHITIS
              DYSPNEA ON EXERTION

| | PRE-BRONCH | | | | POST-BRONCH | | |
|---|---|---|---|---|---|---|---|
| | Pred | Pre | % Pred | # SD | Post | % Pred | % Change |
| LUNG VOLUMES | | | | | | | |
| SVC (L) | 4.64 | 4.88 | 105 | 0.43 | | | |
| RV (Pleth) | 2.01 | 1.42 | 71 | −1.55 | | | |
| TGV (Pleth) | 3.55 | 3.15 | 89 | −0.71 | | | |
| TLC (Pleth) | 6.64 | 6.30 | 95 | −0.51 | | | |
| RV/TLC (Pleth) | 30 | 23 | | | | | |
| TLC (N2) (L) | 6.64 | 4.88 | 73 | −2.63 | | | |
| Alveolar Volume (L) | 6.61 | 7.42 | 112 | 0.98 | | | |
| LUNG MECHANICS | | | | | | | |
| FEV1 (L) | 3.66 | 4.01 | 110 | 0.70 | | | |
| FVC (L) | 4.64 | 4.78 | 103 | 0.25 | | | |
| FEV1/FVC (%) | 79 | 84 | | | | | |
| FEV3 (L) | | 4.65 | | | | | |
| FEF MAX (L/sec) | 8.68 | 13.49 | 155 | 9.08 | | | |
| FEF 25-75% (L/sec) | 3.67 | 3.89 | 106 | 0.88 | | | |
| FEF 75% (L/sec) | 1.48 | 1.83 | 124 | 1.84 | | | |
| MVV (L/min) | 148 | 146 | 99 | 0 | | | |
| Raw (cmH2O/L/s) | 0.2-2.5 | 1.09 | | | | | |
| DIFFUSION | | | | | | | |
| DLCO-unc (ml/min/mmHg) | 33.24 | 28.64 | 86 | | | | |
| DLCO-cor (ml/min/mmHg) | | 28.34 | | | | | |
| DLCO/VA | 4.71 | 3.86 | 82 | −1.16 | | | |

Interpretation: The FVC, FEV1, FEV1/FVC ratio and FEF25-75% are within normal limits. The MVV is within normal limits. The airway resistance is normal. The alveolar volume determined by the single breath diffusing capacity is larger than the total lung capacity. Re-assessment of lung volume measurements is suggested. Lung Volumes are within normal limits. The diffusing capacity is normal.
Pulmonary Function Diagnosis:
Normal Pulmonary Function
This preliminary report should not be used clinically unless reviewed and signed by a physician.

John Smith, M.D.

Lung volume, lung mechanics and diffusion parameters all were found to be within normal limits. However, the lung volume measured by the single breath diffusion method (VA) is indicated as larger than the lung volume measured by plethysmography (TLC), indicating one of these measurements is in error. Thus, in addition to statements from data file 32 indicating normal parameters, a statement is added suggesting re-assessment of lung volume measurements.

While the numbers themselves would suggest this need for further volume measurements, particularly to an experienced physician or other trained expert, someone with less training and experience may not so readily perceive a need. Accordingly, the statement from data base 32 cautions that further testing should be undertaken. Moreover, the caution is provided during testing on terminal 40, or immediately after testing on printer 38 output, so that the patient can be given further testing immediately, rather than informed at a later date of the need for another test.

EXAMPLE II

MEDICAL GRAPHICS
350 OAKGROVE PARKWAY
ST. PAUL, MN 55110
Name: CONSULT   Date: 1/17/86   ID: 110
Age: 32 yr   Sex: M   Height: 178.00 cm   Weight: 48.00 kg
Dr.   Technician:   Room: OP
Pack Years: 0 yr   Years quit: 14 yr   Packs/Day: 0.00
Dyspnea History: Only after Severe exertion

|  | PRE-BRONCH | POST-BRONCH |
|---|---|---|

| LUNG MECHANICS | Pred | Pre | % Pred | # SD | Post | % Pred | % Change |
|---|---|---|---|---|---|---|---|
| FEV1 (L) | 4.12 | 2.53 | 61 | −3.18 | | | |
| FVC (L) | 5.17 | 2.84 | 55 | −4.16 | | | |
| FEV1/FVC (%) | 80 | 89 | | | | | |
| FEV3 (L) | | 2.83 | | | | | |
| FEF MAX (L/sec) | 9.22 | 7.97 | 86 | −2.36 | | | |
| FEF 25-75% (L/sec) | 4.12 | 5.07 | 123 | 3.80 | | | |
| FEF 75% (L/sec) | 1.83 | 2.11 | 115 | 1.47 | | | |

Interpretation: Although the FEV1 and FVC are reduced, the FEV1/FVC ratio is increased.
Conclusions: The reduction in FVC would suggest a concurrent restrictive process. However, the presence of restriction should be confirmed by measurement of lung volumes.
Pulmonary Function Diagnosis:
Moderately severe Restriction -Possible
This preliminary report should not be used clinically unless reviewed and signed by a physician.
John Smith, M.D.

In this case, no lung volume or diffusion information was gathered during testing. Thus, the reduction in FVC is indicated only as suggesting a concurrent restrictive process, and lung volume testing is advised. The diagnostic output from type file 36 is airways restriction, indicated as possible, and also indicated as moderately severe based on the settings in data files 28 and 30.

EXAMPLE III

MEDICAL GRAPHICS
350 OAKGROVE PARKWAY
ST. PAUL, MN 55110
Name: CONSULT   Date: 2/19/86   ID: 185
Age: 67 yr   Sex: M   Height: 188.00 cm   Weight: 94.00 kg
Dr.   Technician:   Room:
Dyspnea History: Only after Severe exertion
Diagnosis: PRE-OP ACB

| | PRE-BRONCH | | | | POST-BRONCH | | |
|---|---|---|---|---|---|---|---|
| | Pred | Pre | % Pred | # SD | Post | % Pred | % Change |
| LUNG VOLUMES | | | | | | | |
| SVC (L) | 5.17 | 2.01 | 39 | −5.64 | 1.98 | 38 | −1 |
| RV (Pleth) | 2.78 | 2.56 | 92 | −0.58 | 2.25 | 81 | −12 |
| TGV (Pleth) | 4.41 | 30.80 | 698 | 47.12 | 2.82 | 64 | −91 |
| TLC (Pleth) | 7.95 | 4.57 | 57 | −5.04 | 4.23 | 53 | −7 |
| RV/TLC (Pleth) | 35 | 56 | | | 53 | | −5 |
| Alveolar Volume (L) | 7.95 | 3.80 | 48 | | | | |
| LUNG MECHANICS | | | | | | | |
| FEV1 (L) | 3.88 | 1.27 | 33 | −5.22 | 1.25 | 32 | −2 |
| FVC (L) | 5.17 | 2.01 | 39 | −5.64 | 1.98 | 38 | −1 |
| FEV1/FVC (%) | 75 | 63 | | | 63 | | 0 |
| FEV3 (L) | | 1.64 | | | | | |
| FEF MAX (L/sec) | 9.65 | 3.58 | 37 | −11.45 | 2.97 | 31 | −17 |
| FEF 25-75% (L/sec) | 3.42 | 0.05 | 1 | −13.48 | 0.60 | 18 | 1100 |
| FEF 75% (L/sec) | 1.21 | 0.16 | 13 | −5.53 | 0.21 | 17 | 31 |
| Raw (cmH2O/L/s) | 0.2-2.5 | 3.12 | | | | | |
| DIFFUSION | | | | | | | |
| DLCO-unc (ml/min/mmHg) | 34.95 | 17.00 | 49 | | | | |
| DLCO-cor (ml/min/mmHg) | | 18.67 | | | | | |
| DLCO/VA | 3.80 | 4.47 | 118 | 0.92 | | | |

INTERPRETATION: The FVC, FEV1, FEV1/FVC ratio and FEF25-75% are reduced indicating airway obstruction. The airway resistance is increased. While the TLC and SVC are reduced, the FRC is high. Following administration of bronchodilators, there is a good response indicated by the increased FEF25-75%. The reduced diffusing capacity indicates a moderately severe loss of functional alveolar capillary surface.

-continued

Conclusions: Severe airway obstruction is present. The diffusion defect, normal FEV1/FVC ratio and reduced FVC suggest an early parenchymal process. The response to bronchodilators indicates a reversible component. In view of the severity of the diffusion defect, studies with exercise would be helpful to evaluate the presence of hypoxemia.
Pulmonary Function Diagnosis: Severe Obstructive Airways Disease-Reversible
Severe Restriction -Parenchymal
Moderately severe Diffusion Defect
This preliminary report should not be used clinically unless reviewed and signed by a physician.
John Smith, M.D.

In this example, the parameters give a superficial indication of emphysema, due to the presence of obstructed airways disease and reduced diffusion. Paradoxical, however, is a significant response to bronchodilators, which would indicate asthma or a reversible component. Thus, a recommendation for studies with exercise is included among the conclusions.

EXAMPLE IV

MEDICAL GRAPHICS
350 OAKGROVE PARKWAY
ST. PAUL, MN 55110
Name: CONSULT   Date: 2/23/86   ID: 250
Age: 34 yr   Sex: M   Height: 184.00 cm   Weight: 67.00 kg
Dr.   Technician:   Room: OP
Diagnosis: ALS

|  | PRE-BRONCH | | | | POST-BRONCH | | |
| --- | --- | --- | --- | --- | --- | --- | --- |
|  | Pred | Pre | % Pred | # SD | Post | % Pred | % Change |
| LUNG VOLUMES | | | | | | | |
| SVC (L) | 5.56 | 4.62 | 83 | −1.68 | | | |
| RV (Pleth) | 1.91 | 1.78 | 93 | −0.34 | | | |
| TGV (Pleth) | 3.85 | 3.95 | 103 | 0.18 | | | |
| TLC (Pleth) | 7.48 | 6.40 | 86 | −1.61 | | | |
| RV/TLC (Pleth) | 26 | 28 | | | | | |
| Alveolar Volume (L) | 7.48 | 5.77 | 77 | | | | |
| LUNG MECHANICS | | | | | | | |
| FEV1 (L) | 4.38 | 1.03 | 24 | −6.70 | | | |
| FVC (L) | 5.56 | 4.45 | 80 | −1.98 | | | |
| FEV1/FVC (%) | 79 | 23 | | | | | |
| FEV3 (L) | | 4.35 | | | | | |
| FEF MAX (L/sec) | 9.79 | 8.19 | 84 | −3.02 | | | |
| FEF 25-75% (L/sec) | 4.19 | 5.57 | 133 | 5.52 | | | |
| FEF 75% (L/sec) | 1.85 | 2.94 | 159 | 5.74 | | | |
| Raw (cmH2O/L/s) | 0.2−2.5 | 0.46 | | | | | |
| DIFFUSION | | | | | | | |
| DLCO-unc (ml/min/mmHg) | 39.46 | 18.25 | 46 | | | | |
| DLCO-cor (ml/min/mmHg) | 39.46 | 22.02 | 56 | | | | |
| DLCO/VA | | 3.16 | | | | | |

Interpretation: The FEV1 and FEV1/FVC ratio are reduced. The airway resistance is normal. Lung Volumes are within normal limits. The reduced diffusing capacity indicates a moderately severe loss of functional alveolar capillary surface.
Conclusions: Although there is severe airway obstruction and a diffusion defect suggesting emphysema, the absence of overinflation indicates a concurrent restrictive process which may account for the diffusion defect. Although bronchodilators were not tested, a clinical trial may be helpful to assess the presence of a reversible component. In view of the severity of the diffusion defect, studies with exercise would be helpful to evaluate the presence of hypoxemia.
Pulmonary Function Diagnosis:
Severe Obstructive Airways Disease
Restriction -Probable
Moderately severe Diffusion Defect
This preliminary report should not be used clinically unless reviewed and signed by a physician.
John Smith, M.D.

There is a severe reduction of flow rates, yet lung volumes are indicated as normal, which should not occur. While severe airway obstruction and diffusion defect suggest emphysema, the absence of over-inflation indicated a concurrent restrictive process (e.g. asbestosis) which may account for the diffusion defect. Accordingly, a statement to this effect is printed among the conclusions, along with a recommendation to administer bronchodilators in further testing.

The text for all of the above examples, including not only direct indications of normality/abnormality, but also conclusions as to nature of the disease, disease types and severity degrees and recommendations for further testing, are generated entirely from statement dictionary 32. A physician reviewing the preliminary diagnosis may or may not modify it. In either event, significant time is saved in avoiding the task of preparing the initial text. The likelihood that editing is necessary is substantially reduced by the fact that the physician can predetermine abnormality parameters and breakpoints as described, and also can modify the wording of statements in the statement dictionary. As a final benefit, the preliminary diagnosis, generated in accordance with modifications to the data files, can warn a technician or physician of a need for further testing based on lack of lung volume testing, a paradoxical bronchodilator response, or the like.

What is claimed is:

1. A pulmonary diagnostic apparatus, including:
a first electronic data storage means, and a plurality of expected values stored in said first data storage means, each expected value representing a predicted normal level for a pulmonary function;
a first data input means for entering a plurality of value ranges into said first data storage means, each of said ranges corresponding to and encompassing one of said expected values, said first data input means including user operable range input means for adjustably determining the ranges corresponding to each expected value whereby each said range represents a pulmonary function at a level within a normal range as determined by the user;
a second data input means for entering a plurality of boundary values into said first data storage means, said boundary values being arranged in sets of consecutively increasing value, each set corresponding to one of said ranges and determining, with respect to its corresponding range, increasing degrees of departure from said range, said second data input means including user operable boundary input means for adjustably determining said boundary values, thereby to determine the degrees of departure corresponding to each range that represent a pulmonary function at increasingly abnormal levels as determined by the user;
a pulmonary function testing means for measuring a plurality of pulmonary functions and providing a plurality of performance values to said first data storage means, each performance value based upon a measured pulmonary function and corresponding to one of said expected values; and
a processing means operatively associated with said first data storage means for comparing each of said performance values with its corresponding one of said value ranges and generating a first output indicating whether or not said performance value is within said corresponding range, said processing means further comparing each of said performance values lying outside of its corresponding range with its corresponding one of said sets of boundary values and generating a second output indicating a degree of departure from the corresponding range.

2. The apparatus of claim 1 further including:
a display means operatively associated with said processing means for presenting said first and second outputs in a form to facilitate user recognition.

3. The apparatus of claim 2 wherein:
each of said ranges is determined by an upper limit greater than the corresponding predicted value and a lower limit less than the predicted value, said upper and lower limits being selectable and adjustable by the user, and wherein said degrees of departure are defined by preselection of increasing, discrete levels for a quantity B determined in accordance with the formula $$B = 10(1 - M/L)$$

where B is the extent of departure, M is the measured performance value and L is the one of said upper and lower limits nearest the measured performance value.

4. The apparatus of claim 3 further including:
a second data storage means operatively associated with said processing means, and a plurality of degree of severity labels stored in said second storage means, each corresponding to one of said degrees of departure, wherein said processing means selects one of said degree of severity labels in accordance with the determined degree of departure and generates said selected label as said second output.

5. The apparatus of claim 4 including:
a third storage means operatively associated with said processing means and a plurality of pulmonary condition diagnostic labels stored in said third data storage means, wherein said processing means generates said second output by generating a selected one of said diagnostic labels along with the selected degree of severity label in accordance with the particular ones of said measured performance values outside of their associated ranges, and the degree of severity of each of said particular measured performance values.

6. The apparatus of claim 4 including:
a data entry means connected with said second storage means and operable by said user for modifying said degree of severity labels.

7. The apparatus of claim 6 further including:
a fourth storage means operatively associated with said processing means and a plurality of textual statements relating to diagnosis of pulmonary condition stored in said fourth storage means, said processing means selecting at least one selected statement of said textual statements in accordance with particular ones of said measured performance values outside of their associated ranges and the degree of abnormality of each said particular measured performance value, and generates each said selected statement as a third output.

8. The apparatus of claim 7 wherein:
said data entry means for selectively modifying said textual statements comprises a keyboard operatively connected to said fourth storage means.

9. The process for preliminarily diagnosing pulmonary condition, including the steps of:
providing a plurality of first signals, each representing an expected performance value corresponding to a pulmonary function at a normal level;
adjustably fixing an upper limit value greater than each of said expected values, and a lower limit value less than each of said expected values, thereby to define a normal range of values corresponding to and encompassing each expected value and including all values between and including the corresponding upper and lower limits;
measuring a plurality of pulmonary functions to generate a plurality of performance signals, each representing a measured performance value corresponding to one of said expected values and to one of said ranges;
defining the extent of departure of each of said measured performance values from the corresponding one of said ranges, in accordance with the formula $$B = 10(1 - M/L)$$

where B equals the extent of departure; M equals the measured performance value; and L equals the one of said upper and lower limits nearest the measured performance value;
comparing each measured performance value with the corresponding upper and lower limits; and generating a first output indicating whether each of said measured performance values lies within or outside of its associated one of said ranges, and generating a second output for each measured value outside of its associated range indicating the extent of departure from said associated range.

10. The process of claim 9 including the further step of:

adjustably selecting a plurality of designated values for B arranged in order of increasing value, to divide the extent of departure into discrete degrees of severity corresponding to ranges in the value of B based on each of said designated values.

11. The process of claim 10 including the further step of:

providing a degree of severity label associated with each of said designated values and generating one of said degree of severity labels as said second output, in accordance with the extent of departure.

12. The process of claim 11 including the further step of:

providing a plurality of diagnostic labels representative of pulmonary conditions, and selecting at least one of said diagnostic labels for use with one of said degree of severity labels in providing said second output.

13. The process of claim 12 wherein said step of providing said diagnostic labels includes the step of selecting said diagnostic labels in accordance with the particular ones of said measured performance values outside of their associated ranges, and further in accordance with the degree of severity of said particular measured values.

14. The process of claim 13 including the further step of:

providing a plurality of first textual statements describing either the normality or abnormality of one of said measured performance values, and selecting at least one of said first textual statements as said first output in accordance with the ones of said measured performance values found to be abnormal.

15. The process of claim 14 including the further step of:

providing a plurality of second textual statements concerning pulmonary conditions, and selecting at least one of said second textual statements as a third output dependent upon the ones of said measured performance values found to be abnormal and the degree of abnormality.

16. The process of claim 9 wherein the step of comparing each measured performance value with the corresponding upper and lower limits includes the following steps, in sequence:

(a) determining the presence of obstructive airways disease (OAD) based on the following mathematical algorithm:

$$\text{OAD degree} = FEV_1/FVC + (FEF\ 25\text{-}75\%/5) + (FEF\ 75\%/20)$$

where FVC is the forced vital capacity, $FEV_1$ is the forced expiratory volume at one second of FVC, and FEF is the forced expiratory flow over 25–75% and at 75% of FVC, respectively;

(b) determining the presence of measured diffusion performance values, and identifying such diffusion performance values, if present, as normal, increased or reduced;

(c) determining the presence of lung volume measured performance values, and identifying any such values as normal, increased or reduced; and (d) determining the presence of measured performance values responsive to administration of a bronchodilator, and determining any such values to indicate a response that is either significant, not significant, or paradoxical.

* * * * *